(12) United States Patent
Burris (10) Patent No.: US 7,750,815 B2
(45) Date of Patent: Jul. 6, 2010

(54) PORTABLE MONITORING APPARATUS WITH OVER THE AIR PROGRAMMING AND SAMPLING VOLUME COLLECTION CAVITY

(75) Inventor: Sanford A. Burris, Kirtland, OH (US)

(73) Assignee: Quantum Electronics Ltd., Eastlake, OH (US)

( * ) Notice: Subject to any disclaimer, the term of this patent is extended or adjusted under 35 U.S.C. 154(b) by 320 days.

(21) Appl. No.: 12/035,939

(22) Filed: Feb. 22, 2008

(65) Prior Publication Data

US 2009/0212957 A1 Aug. 27, 2009

(51) Int. Cl.
G08B 23/00 (2006.01)
(52) U.S. Cl. .............. 340/573.4; 340/573.1; 340/539.1; 340/539.11; 340/539.12; 340/825.69
(58) Field of Classification Search .............. 340/573.4, 340/573.1, 539.1, 539.11, 539.12, 825.69; 128/903, 920; 600/300, 301; 701/211, 212
See application file for complete search history.

(56) References Cited

U.S. PATENT DOCUMENTS

| 5,220,919 | A | 6/1993 | Phillips et al. |
| 5,731,757 | A | 3/1998 | Layson, Jr. |
| 5,944,661 | A | 8/1999 | Swette et al. |
| 5,959,533 | A | 9/1999 | Layson, Jr. et al. |
| 6,014,080 | A | 1/2000 | Layson, Jr. |
| 6,774,799 | B2 | 8/2004 | Defant et al. |
| 6,881,582 | B2 | 4/2005 | Ratogi et al. |
| 6,886,653 | B1 | 5/2005 | Bellehumeur |
| 6,405,213 | B1 | 6/2008 | Layson et al. |
| 7,382,247 | B2 * | 6/2008 | Welch et al. ........... 340/539.12 |
| 7,515,043 | B2 * | 4/2009 | Welch et al. ........... 340/539.12 |
| 2003/0222781 | A1 | 12/2003 | Defant et al. |

* cited by examiner

*Primary Examiner*—Hung T. Nguyen
(74) *Attorney, Agent, or Firm*—Anthony M. Del Zoppo, III; Driggs, Hogg, Daugherty & Del Zoppo Co., LPA (57) ABSTRACT

A portable monitoring apparatus includes a bracelet having a housing and a strap for connecting the bracelet with a body part of a person being monitored, and an electronic monitoring circuit disposed in the housing. The electronic monitoring circuit executes an executable program for controlling the monitoring circuit according to a control algorithm. The executable program is modifiable by over the air programming from a monitoring network having transmitting and receiving circuits in operative communication with the electronic monitoring circuit. The housing of the bracelet includes a contract portion configured to engage the skin of the person being monitored and a cavity portion having an opening defining a closed sampling volume when the base is in contact with the person. An alcohol sensor is disposed at the sampling volume for detecting a physiological condition of the human and generating a signal thereof.

12 Claims, 13 Drawing Sheets

PORTABLE MONITORING APPARATUS WITH OVER THE AIR PROGRAMMING AND SAMPLING VOLUME COLLECTION CAVITY

BACKGROUND OF THE INVENTION

1. Field of the Invention

The present application relates to the art of electronic monitoring of persons and their activities and, more particularly, to collecting and storing physiological information and other information and data regarding the humans being monitored. The preferred embodiments of the present application will be described in connection with methods and apparatus for monitoring and collecting data relating to criminal offenders, specifically data on alcohol use by the offenders, and, accordingly, the primary focus will be placed on alcohol and/or ethanol sensing and data collection techniques. However, it is to be appreciated that the preferred embodiments have other uses and provide advantages in other applications such as, for example, in monitoring criminal and non-criminal persons and collecting physiological and other data relating to those persons for use in parole compliance reporting and recording, medical studies, medicament usage compliance, and a wide variety of other reasons.

2. Description of Prior Art

Many systems are currently available for determining the location of subjects, such as criminal offenders and victims by means of electronic monitoring at fixed locations, such as at the subject's residence. These systems are commonly known as "house arrest" systems and they typically utilize a body-worn device which typically transmits a signal to a receiver powered by an electrical outlet communicating to a central monitoring service over a standard telephone line hardwired at the offender's residence.

Such house arrest systems are useful when offenders are sentenced in a criminal proceeding to remain within the confines of their own residence for a period of time specified in the sentence. This reduces the demands placed upon the already crowded penal system while enabling the courts to supervise these individuals through parole departments by using remote electronic means. However, for certain other crimes such as drug or alcohol use, the sentencing may impose restrictions only on the further consumption of drugs or alcohol without imposing such geographical limitations. Domestic crime sentences may impose geographical limitations which restrict access to single residences, for example. Accordingly, highly portable tracking and monitoring devices have been proposed for monitoring the activities of criminal or other offenders while enabling them to rejoin society in a productive way such as during work and family hours.

One such highly mobile system but without drug or alcohol sensing capabilities is taught in U.S. Pat. No. 6,014,080 wherein a tamper resistant body-worn tracking device is provided for use by offenders or potential victims in a wireless communication system receiving signals from a global positioning system (GPS). The tracking device directly communicates special coordinates to multiple remote sites. The tracking device is an enclosed case worn on a limb of a person. The case contains a battery, a signaling device, and a circuit board containing a field programmable gate array, a wireless data modem, a conventional GPS receiver, and a matched filtering GPS receiver.

Another example is taught in U.S. Pat. No. 5,731,757. There, a portable locator or tracking apparatus for continuous location determination of subjects communicates with a body-worn, non-removable, tamper resistant transceiver and a central database system. In this system, a wireless network cell site processes wireless signals and switches the communication through a mobile switching office to a public switched telephone network. The communication from the subject's portable tracking device is routed to a central database system where response decisions for notification to parole and probation officers, victims, and other law enforcement officials are made based on schedule rules and location constraints provided by a supervising agency such as a parole or probation board. Essentially, an "electronic fence" is downloaded into the portable tracking device worn by the offender wherein the offender's movements within the area defined by the fence can be determined and logged so that appropriate alarms may be generated if the offender wanders from the predefined zone.

Systems of the type described above have met with some success. Other systems have been proposed as well wherein an emphasis is made towards sensing the alcohol consumption activities of the device wearer. However, there exists a need for improved monitoring systems of the type described above such as monitoring systems having a monitoring network with the ability to selectively interrogate each of the portable monitoring apparatus within the network from a central location substantially in real time and as deemed necessary or desired such as to determine whether a subject has consumed alcohol and, further, with the ability to distribute and initiate software upgrades to the operating systems of the respective portable monitoring apparatus or to other software components or modules such as algorithms, for example, within the system. The former improvement provides an ease of use of the overall system and the latter improvement ensures a uniformity throughout the system and can provide enhanced performance or improved functional compliance. In addition, there exists a need for an improved portable monitoring apparatus which has an enhanced ability to detect one or more specific conditions of the offender being monitored. Still further, there exists a need to improve the mechanical construction of the portable monitoring apparatus worn by the criminal offenders such as by providing an improved tamper evident band secured about a portion of the offenders body.

SUMMARY OF THE INVENTION

Methods and apparatus are provided in the present application which overcome deficiencies in prior art systems and provide advantages thereover. In one form, a monitoring system including an electronic monitoring circuit contained within an ankle-worn bracelet is in operative communication with a monitoring network which selectively interrogates the electronic monitoring circuit for determining a version of executable software in the circuit and downloads updated executable operating system software as necessary. The monitoring network is further configured to selectively initiate or force data collection operations in the electronic monitoring circuit. The bracelet includes a housing having a base with a cavity portion with an opening defining a closed sampling volume for use with an alcohol sensor device.

The monitoring system monitors physiological conditions of an associated human and includes a bracelet having a housing and a strap for connecting the bracelet with a body part of the associated human being monitoring, an electronic monitoring circuit disposed in the housing, and a monitoring network in operative communication with the electronic monitoring circuit, the monitoring network having at least one receiving circuit and at least one transmitting circuit. The electronic monitoring circuit disposed within the housing of the bracelet includes one or more sensors for detecting the conditions of the human being monitored and for generating signals based on the detected conditions. The electronic monitoring circuit further includes first and second memories, the first memory storing a first executable program defining a first control algorithm, and the second memory storing data relating to the condition of the human being monitored. A processor portion of the electronic monitoring circuit is operatively coupled with the first sensor and with the first and second memories. The processor is configured to execute the first executable program for controlling the electronic monitoring circuit according to the first control algorithm to generate condition data based on the first signal and relating to the detected conditions of the human being monitored and to store the condition data in the second memory. The electronic monitoring circuit further includes a transmitter and a receiver. The transmitter is operatively associated with the processor for selectively transmitting the condition data from the housing as a first transmitted signal. The receiver of the electronic monitoring circuit is operatively associated with the processor for selectively receiving a command signal as a first received signal. In the monitoring network, the receiving circuit receives the first transmitted signal from the electronic monitoring circuit. The transmitting circuit of the monitoring network transmits the command signal. The processor of the electronic monitoring circuit is responsive to the command signal from the monitoring network to execute a second executable program different from the first executable program for controlling the electronic monitoring circuit according to a second control algorithm different from the first control algorithm.

In one preferred form, the monitoring network includes a mobile cellular communication device, such as a cell phone, adapted to be carried by the associated human being monitored, and a central monitoring station having a server and a database storing the condition data and the second executable program.

In another preferred form, the processor of the electronic monitoring circuit contained within the bracelet is configured to replace the first executable program in the first memory with the second executable program transmitted from the monitoring network, based on the command signal from the monitoring network. Thereafter, the electronic monitoring circuit contained within the bracelet executes the second executable program, thereby updating a software version of the executable operating system of the electronic monitoring circuit contained within the bracelet. The second executable program is executed for controlling the electronic monitoring circuit according to the second control algorithm different from the first control algorithm.

In another embodiment, a bracelet device is provided for use in a monitoring system for monitoring a condition of an associated human. The bracelet device includes a housing and an electronic monitoring circuit disposed in the housing. The housing includes a base with a contact portion configured on a first side to engage skin of the associated human, and a cavity portion having an opening on the first side. The opening selectively defines a closed sampling volume when the first side of the contact portion of the housing is held in contact with the skin of the associated human. The electronic monitoring circuit includes a first sensor, first and second memories, a processor, a transmitter, and a receiver. The first sensor is disposed at the sampling volume for detecting a condition of the human and for generating a first signal based on the detected condition. The first memory stores a first executable program defining a first control algorithm. The second memory stores data relating to the condition of the human being monitored. The processor is operatively coupled with the first sensor and with the first and second memories and is configured to execute the first executable program contained within the first memory for controlling the electronic monitoring circuit according to the first control algorithm. The processor executes the first control algorithm to generate condition data based on the first signal and relating to the detected condition of the human being monitored and to store the condition data in the second memory. The transmitter and receiver are operatively associated with the processor. The transmitter selectively transmits the condition data from the housing as a first transmitted signal and the receiver selectively receives a command signal from the associated monitoring system as a first received signal.

As will be realized, the invention is capable of other and different embodiments and its several details are capable of modifications in various respects, all without departing from the invention. Accordingly, the drawings and description are to be regarded as illustrative and not restrictive.

BRIEF DESCRIPTION OF THE DRAWINGS

The invention may take physical form in certain parts and steps and arrangements of parts and steps, the preferred embodiments of which will be described in detail in the specification and illustrated in the accompanying drawings hereof and wherein.

DETAILED DESCRIPTION OF THE PREFERRED EMBODIMENTS

Figure 1:
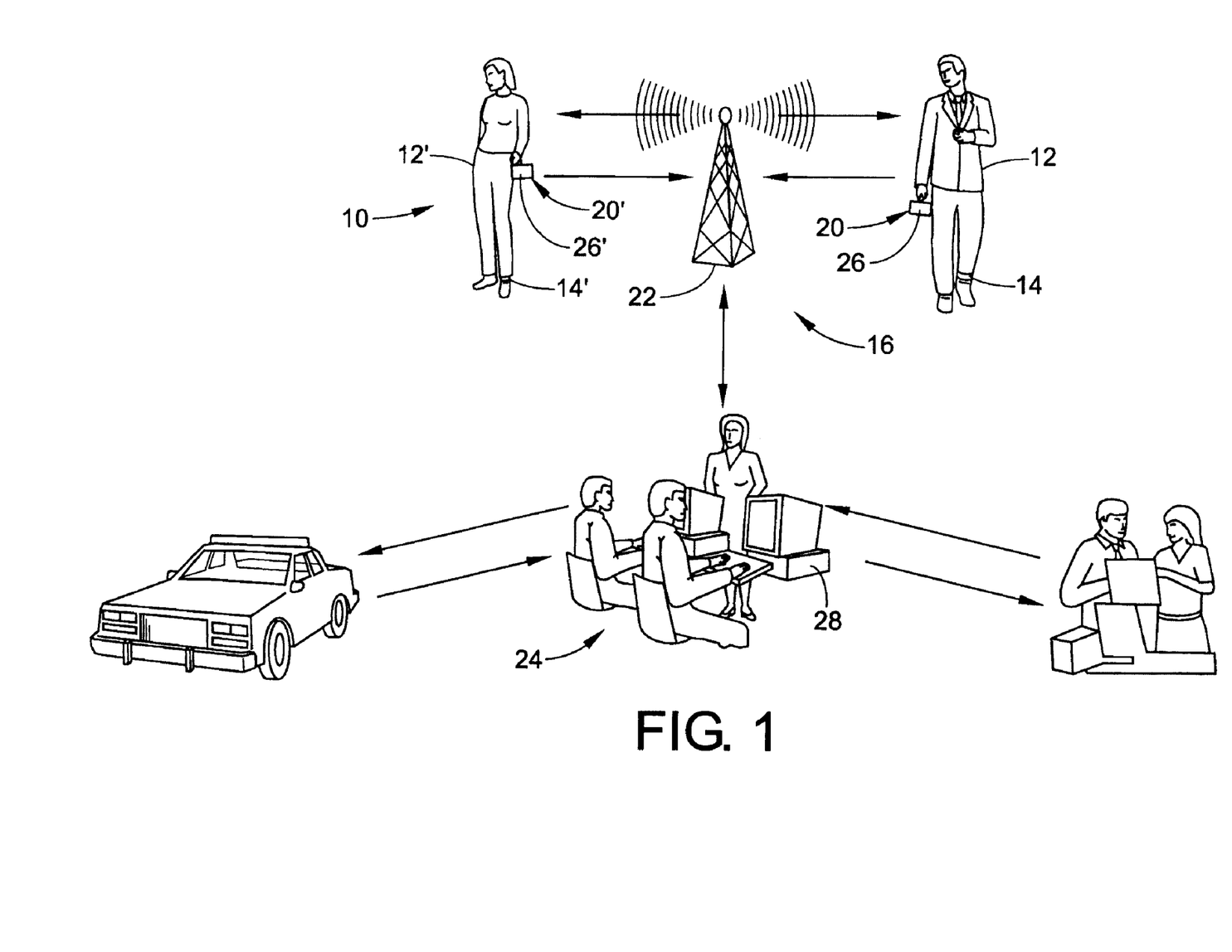
FIG. 1 is a diagram showing the major components of the monitoring system for monitoring selected physiological conditions of an associated human.

With reference now to the drawings wherein the showings are for purposes of illustrating the preferred embodiments of the invention only and not for purposes of limiting same, FIG. 1 is an overall system view of the monitoring system 10 for monitoring a condition of an associated human 12. In its preferred form, the monitoring system 10 includes, essentially, a portable monitoring apparatus 14 adapted for selective connection with the human 12, and a monitoring network 16 adapted for selective communication with the portable monitoring apparatus 14 in a manner to be described in greater detail below. The human 12 is fitted with the portable monitoring apparatus 14 so that it can be worn as the human participates in day to day activities. However, in order to effect monitoring of the human for purposes of determining a condition of the human such as, for example, the use of alcohol, the portable monitoring apparatus 14 includes a plurality of sensors to be described in greater detail below for collecting signals stored as data representative of a behavior of the human for communication thereof to the monitoring network 16.

In the embodiment illustrated, the monitoring network 16 includes a mobile cellular communication device 20 adapted to be carried by the associated human 12 being monitored, a plurality of wireless network cell sites 22 (only one illustrated) in operative communication with a central monitoring station 24. The mobile cellular communication device 20 is preferably a standard cell phone 26 provided with a means for communication with the portable monitoring apparatus 14 such as, for example, using blue tooth technology. The central monitoring station 24 includes one or more servers 28 provided with one or more databases storing the condition data acquired from the human 12 by the portable monitoring apparatus 14 in a manner described below. Overall, however, the wireless network cell sites 22 process the signals from the mobile cellular communication device 20 using well known techniques. It is to be appreciated that several body worn apparatus 14, 14', . . . and communication devices 20, 20', . . . may be included in the monitoring network 16 on a corresponding set of humans 12 being monitored. In FIG. 1 and the other drawing figures, like or similar elements will be represented with a prime (') suffix such as, for example, the first human 12 and the second human 12'. Only two humans are shown wearing the portable monitoring apparatus 14 but the system 10 is useful to monitor hundreds or thousands of humans, each fitted with a monitoring apparatus 14 and mobile communication device 20. Also, it is to be appreciated that the functionality of the mobile cellular communication devices 20 may be integrated into the portable monitoring apparatus 14 to provide a single unitary device on the humans 12 and in communication with the cell sites 22.

Figure 2A:
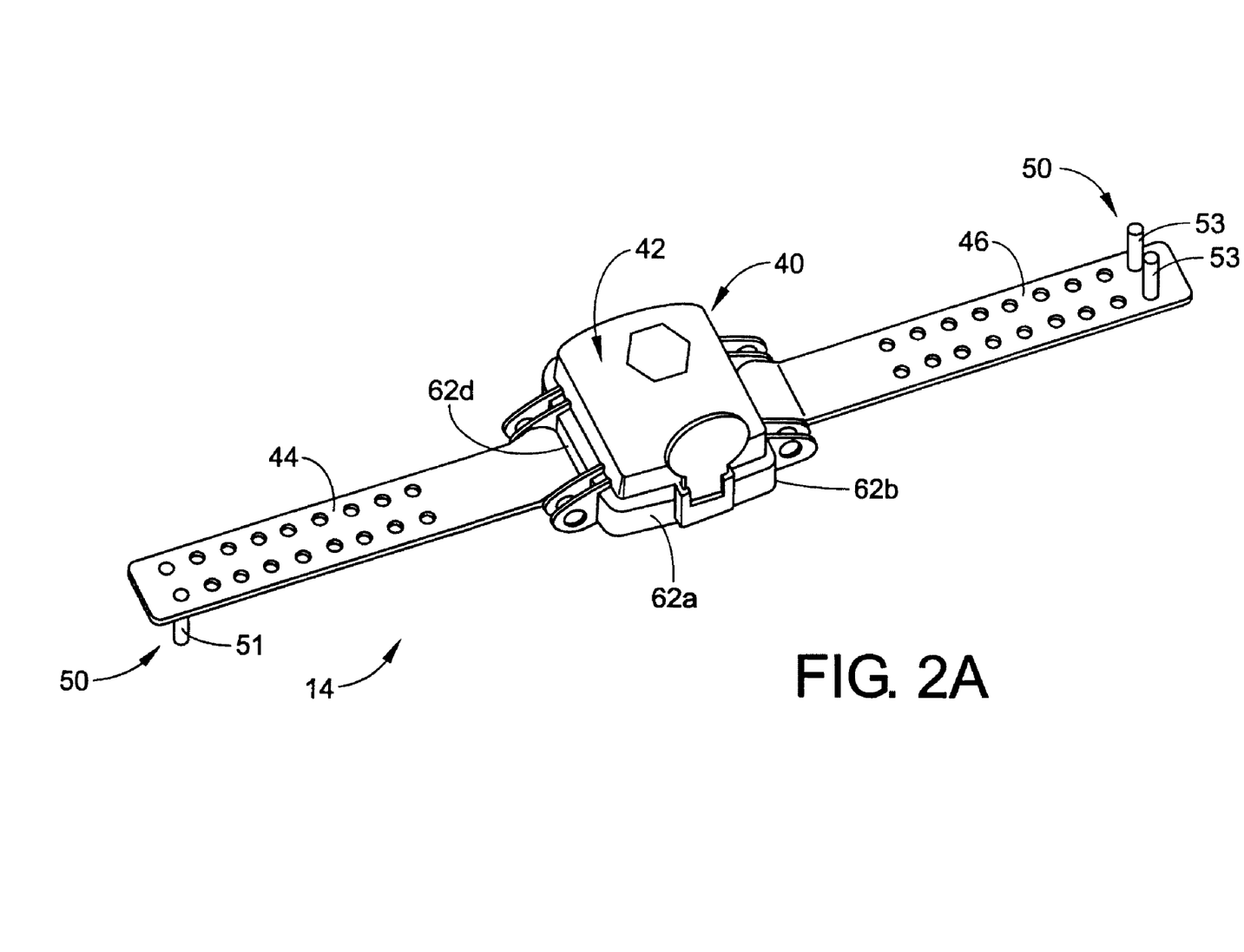
FIGS. 2A and 2B are perspective views showing the top and bottom, respectively, of the portable body worn monitoring apparatus.
Figure 2B:
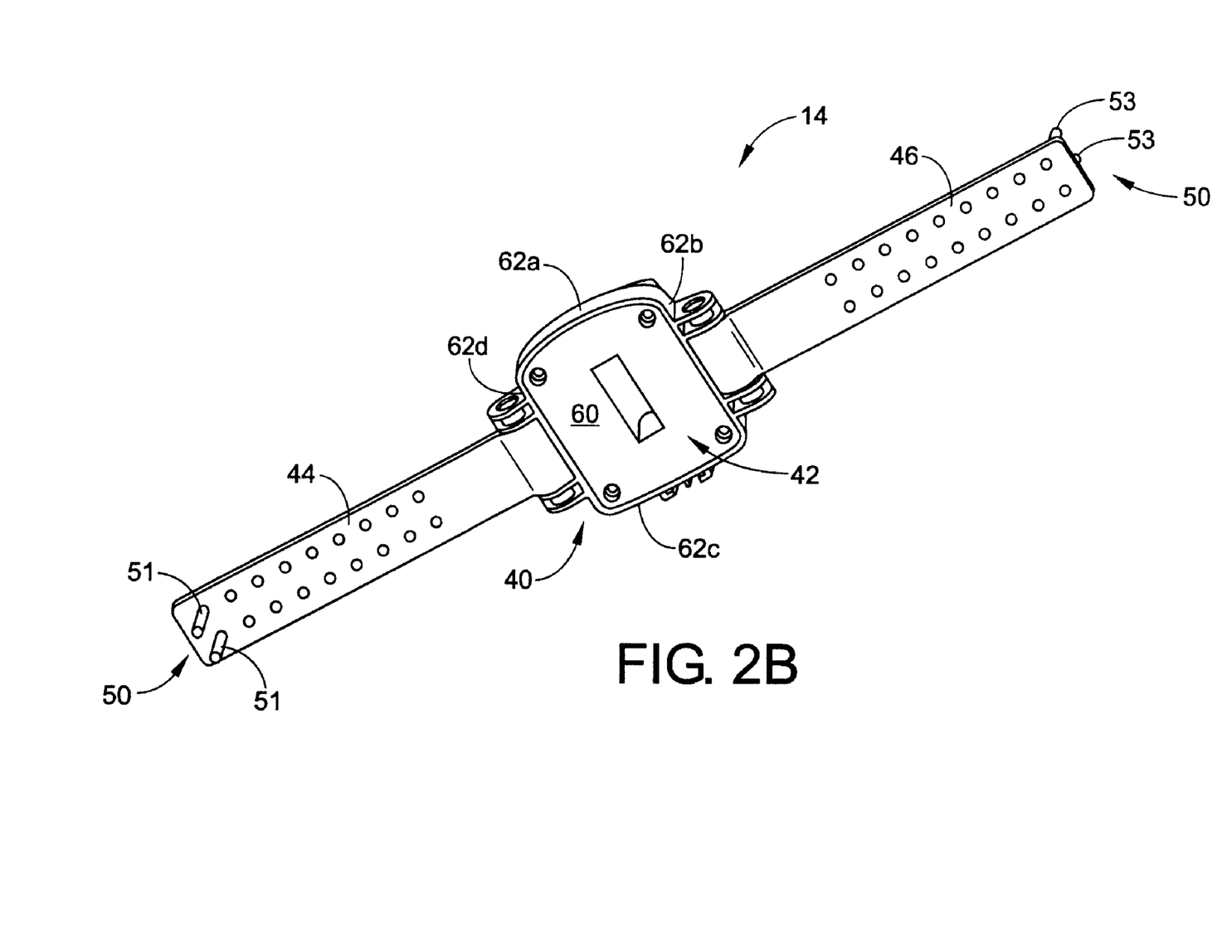

FIGS. 2A and 2B show top and bottom perspective views, respectively, of the portable body worn monitoring apparatus 14 formed in accordance with a preferred embodiment. Referring now to those figures, the apparatus 14 is provided in the form of a body-worn bracelet 40 having a central housing portion 42 and a pair of outwardly extending intermateable straps 44 and 46 for wrapping around the ankle of the human for carrying the housing 42 in close contact with the human's skin. Preferably, the housing 42 is made from a high impact plastic so that it can be safely worn by the human during day to day activities. The straps 42, 46 are formed of a resilient rubberized material so that they can be slightly stretched while attaching the housing onto the human's ankle to be sure that good contact is made therebetween. The straps can be easily washed and cleaned between use on different human subjects. In addition, a tamper-evidence device 50 is provided for locking overlapping ends of each strap 44, 46 together in a fashion using a pair of pins 51 and posts 53.

Generally, as can be seen in the drawings, the housing 42 has an overall square shape in cross-section. The housing has a base 60 and a set of upward sidewalls 62a-62d defining a housing area 64 therebetween, and a removable lid member 66 (FIG. 3) selectively secured onto the sidewalls for closing in the housing area 64.

Figure 3:
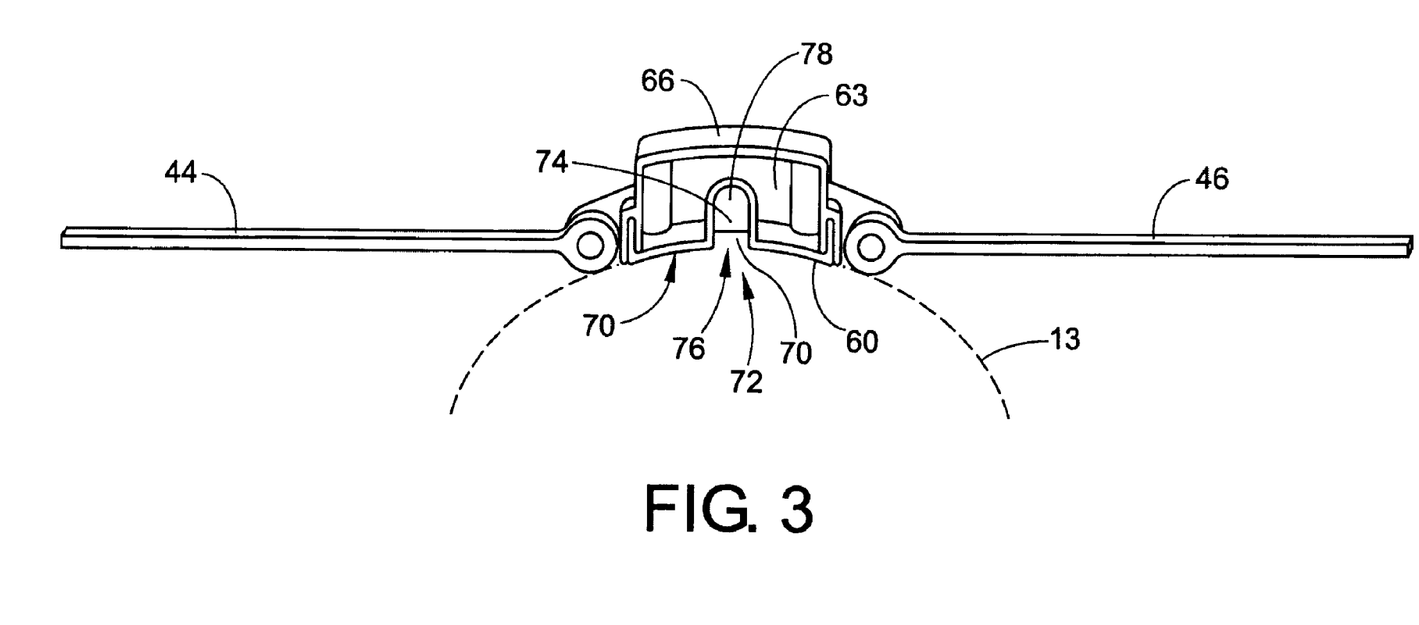
FIG. 3 is a cross-sectional view of the portable monitoring apparatus taken through line 3-3 of FIG. 2B.

As best shown in FIGS. 2B and 3, the base 60 of the housing 42 includes a contact portion 70 forming a radius adapted to confirm with the shape of the leg of the human being monitored. Overall, as can be seen, the contact portion 70 has an overall concave shape in a direction toward the human being monitored. Although the leg is a preferred attachment location, it is to be understood that the contact portion can be modified in many ways to adapt the housing 60 for placement on other portions of the subject's body such as, for example, the wrist, waist or the like.

With particular reference to FIG. 3, a central region 72 of the contact portion 70 forms a cavity 74 having an opening 76 on a first side. The opening 70 selectively defines a closed sampling volume 78 when the first side of the contact portion 70 is held in contact with the skin 13 of the human 12 being monitored. The closed sampling volume 78 is for purposes of providing a region for ethanol contained in the human's skin to evaporate from the skin for collection adjacent a suitable sensor disposed within the cavity 74. The cavity 74 has a preferred volume of approximately $10 \times 10 \times 10$ mm$^3$.

Figure 4:
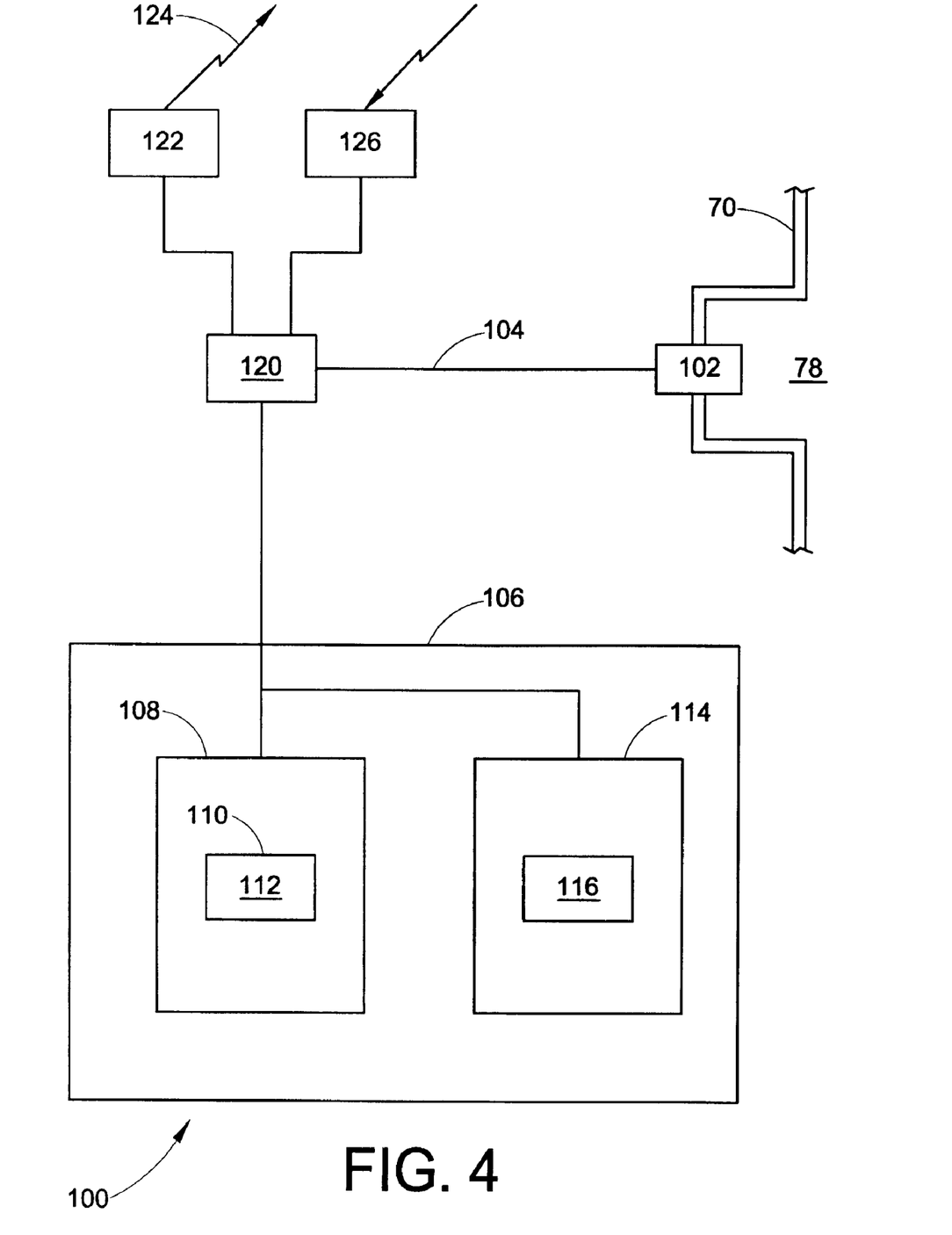
FIG. 4 is a functional block diagram of the electronic monitoring circuit contained within the portable monitoring apparatus of FIGS. 1-3.

It is to be appreciated that the housing 42 carries an electronic monitoring circuit 100 within the housing area 64. FIG. 4 is a functional block diagram illustrating the preferred form of the electronic monitoring circuit 100. With reference thereto, the circuit includes a first sensor 102 for detecting a condition of the human being monitored. Preferably, the first sensor is an alcohol sensor of the type with an electro-chemical fuel cell available from Draggerwerk of Germany although other sensors may be used as well. The first sensor 102 generates a first signal 104 based on the detected condition. The sensor 100 is illustrated in schematic form in FIG. 4 extending into the closed sampling volume 78 formed by the cavity 74 of the housing 42 discussed above. In that way, a portion of the sensor 102 is in communication with the closed sampling volume 78 for generating a signal 104 based on a condition detected within the sampling volume. Preferably, the sensor detects ethanol. Also, preferably, the sensor is held in a spaced relationship relative to the skin 13 of about 5-15 mm. This spaced relationship enables the sensor to detect gasses emitted through the skin and from evaporating sweat of the subject human, thus providing an enhanced and more accurate determination of alcohol use or consumption.

With continued reference to FIG. 4, the electronic monitoring circuit 100 includes a memory 106 with a first memory portion 108 storing first executable program 110 defining a first control algorithm 112. The memory 106 also includes a second memory 114 storing data 116 relating to the condition of the human being monitored. A processor 120 is operatively coupled with the first sensor 102 and with the first and second memory portions 108, 114. The processor is configured to execute the first executable program 110 for controlling the electronic monitoring circuit 100 according to the first control algorithm 112 to generate the condition data 116 based on the first signal 104 and relating to the detected condition of the human being monitored. The processor 120 stores the condition data 116 thereby acquired into the second memory 114. The first executable program 110 includes an embedded operating system component which may be a real-time operating system (RTOS) and other components executable to cause the monitoring circuit to function in a manner described herein. These other components may include software and/or firmware algorithm modules, for example, or other code executable or used during execution while the circuit is in use.

With yet continued reference to FIG. 4, the electronic monitoring circuit 100 includes a transmitter 122 in communication with the processor 120 selectively transmitting the condition data 116 from the electronic monitoring circuit and housing as a first transmitted signal 124. Further, a receiver 126 is operatively associated with the processor 120 for selectively receiving an associated command signal from the monitoring network 16. In their preferred form, the transmitter and receiver 122, 126 are Bluetooth enabled hardware integrated circuit components.

Figure 5:
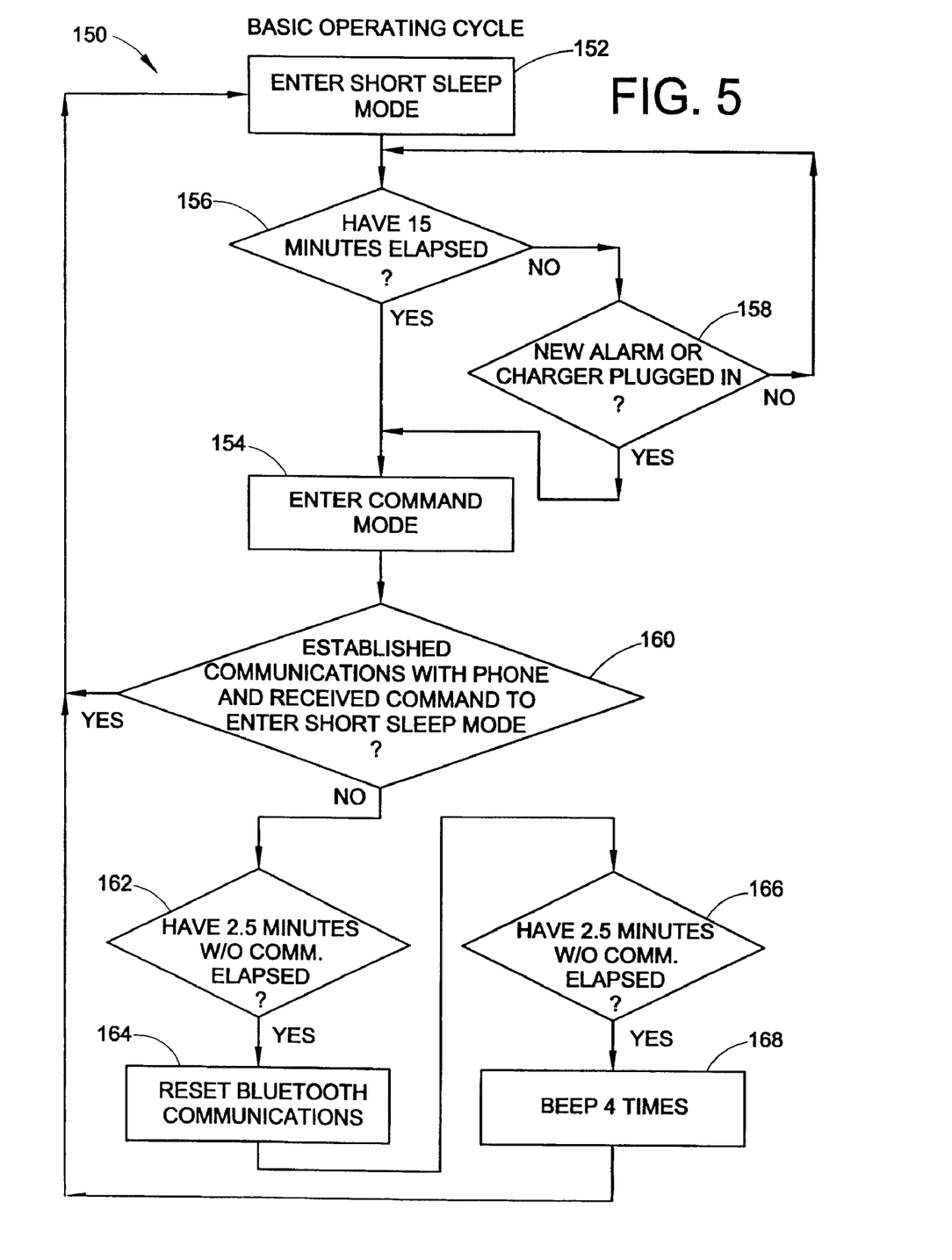
FIG. 5 is a flow chart of the method of operation of the portable body worn monitoring apparatus.

Referring next to FIG. 5, the preferred method of operating the portable monitoring apparatus 14 in accordance with the first executable program 110 of the present exemplary embodiment will be described. In accordance with the method 150, the system operates substantially in a pair of operational modes including a short sleep mode 152 and a command mode 154. As shown in the Figure, the method exits from the short sleep mode 152 every 15 minutes in a test block 156. As will be described below in greater detail in connection with the short sleep mode and with reference to FIG. 6, the timing test block 156 is executed once every 5 seconds. In the event that a total lapsed time between entering the command mode has not yet reached 15 minutes, an alarm test block 158 is executed. If no alarms have been set, the control method 150 returns to the short sleep mode 152.

With continued reference to FIG. 5, the command mode 154 is entered when either of an elapsed time exceeds 15 minutes or an alarm is generated. In the command mode, a set of procedures are executed as will be described below with reference to FIG. 7. Thereafter, the control method 150 determines communications with the associated cellular phone 26 has been established and, if the communication was properly established and the command mode was properly received from the monitoring network 16, the control method 150 returns to the short sleep mode 152. However, if the test at block 160 determines that a communication with the phone system was not established and the command to enter the short sleep mode was not received, a delay loop 164 is executed to wait approximately 2.5 minutes whereupon, if the communication is not yet established, the transmitter 122 and receiver 126 within the electronic monitoring circuit 100 are reset at block 164. Thereafter, at test block 166, if the communication channel is not yet reestablished, the control algorithm 150 executes an audible signal at step 168 for purposes of alerting the human 12 that a significant communication error has occurred.

Figure 6:
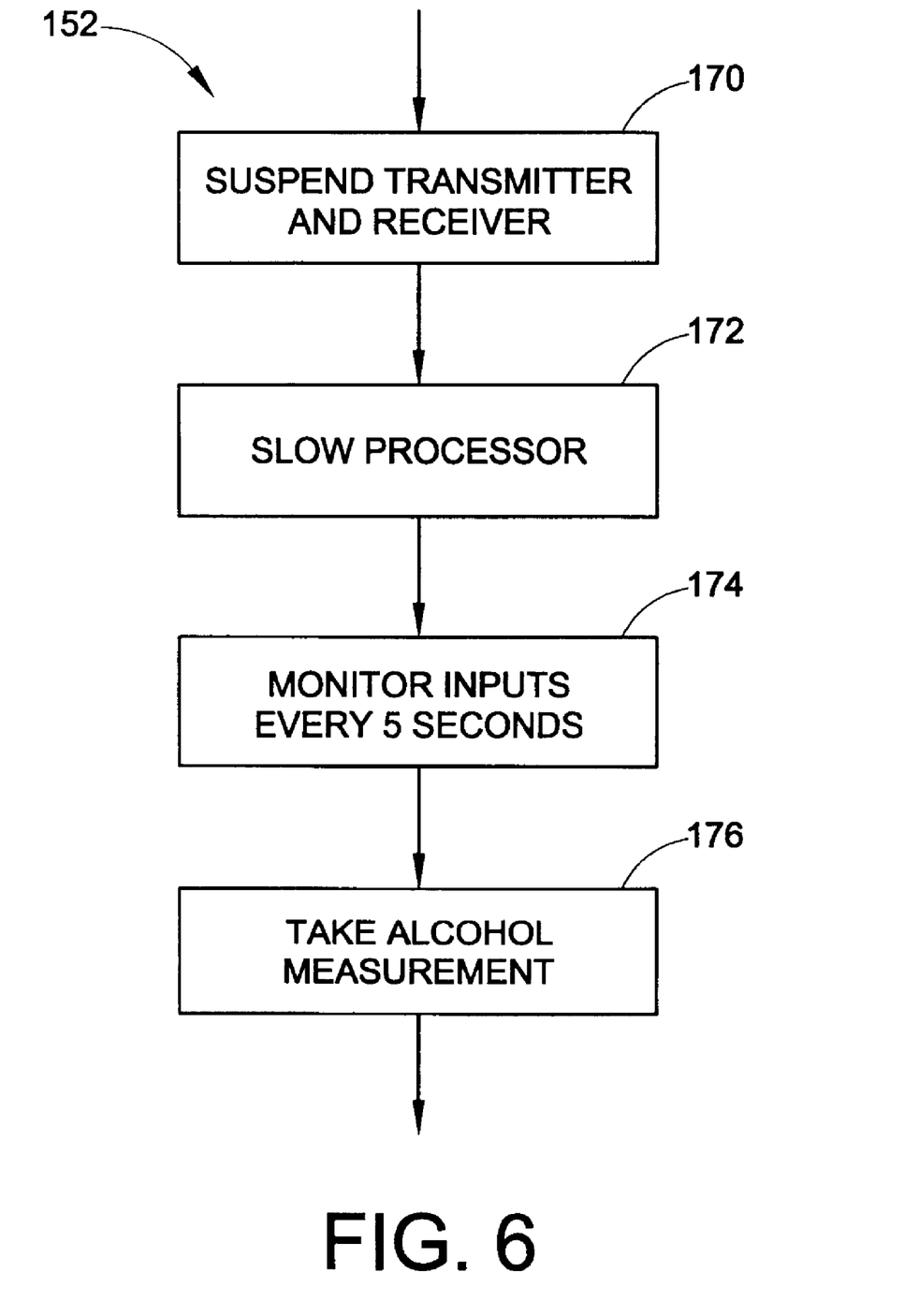
FIG. 6 is a flow chart of a short sleep mode subroutine of the method of FIG. 5.

FIG. 6 illustrates the method executed during the short sleep mode 152 in accordance with the preferred embodiment. With reference thereto, a first step 170 in the short sleep mode suspends activation of the transmitter 122 and receiver 126 circuits for purposes of conserving the battery of the portable monitoring apparatus 14. For further conserving battery life, the clock rate for the processor 120 is reduced to a sub-megahertz range at step 172. Next, all of the inputs associated with the circuit 100 are monitored once every 5 seconds in a reduced monitoring step 174. In step 176, alcohol measurements are not taken as the device 102 is not monitored.

Figure 7:
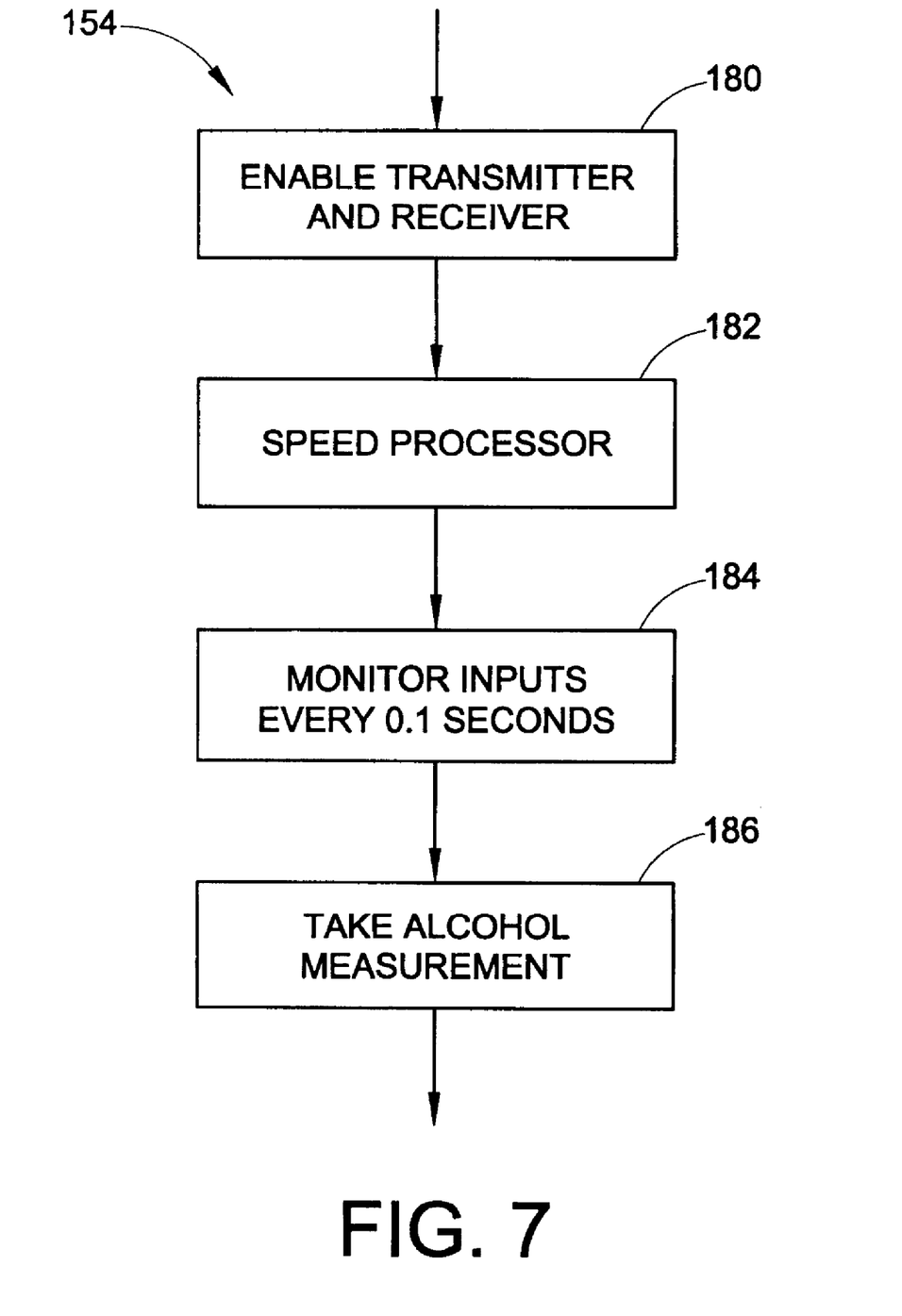
FIG. 7 is a command mode subroutine of the method of a operation of FIG. 5.

In FIG. 7, the command mode 154 executes a step 180 for enabling the transmitter and receiver circuits 122, 126. In the preferred embodiment, this enables Bluetooth communication between the electronic monitoring circuit 100 and the mobile cellular communication device 20. At step 182, the clock rate of the processor 120 is accelerated to several megahertz for higher processing power required for handling the communication protocol and data logging functions. At step 184, all of the inputs associated with the electronic monitoring circuit 100 are enabled and are monitored approximately 10 times per second. Further, at step 186, alcohol measurements are taken and updated once every 15 minutes by enabling the alcohol sensor 102 and by acquiring the signal 104 processing it and storing the results of the processing as condition data 116 in the second memory 114.

Figure 8:
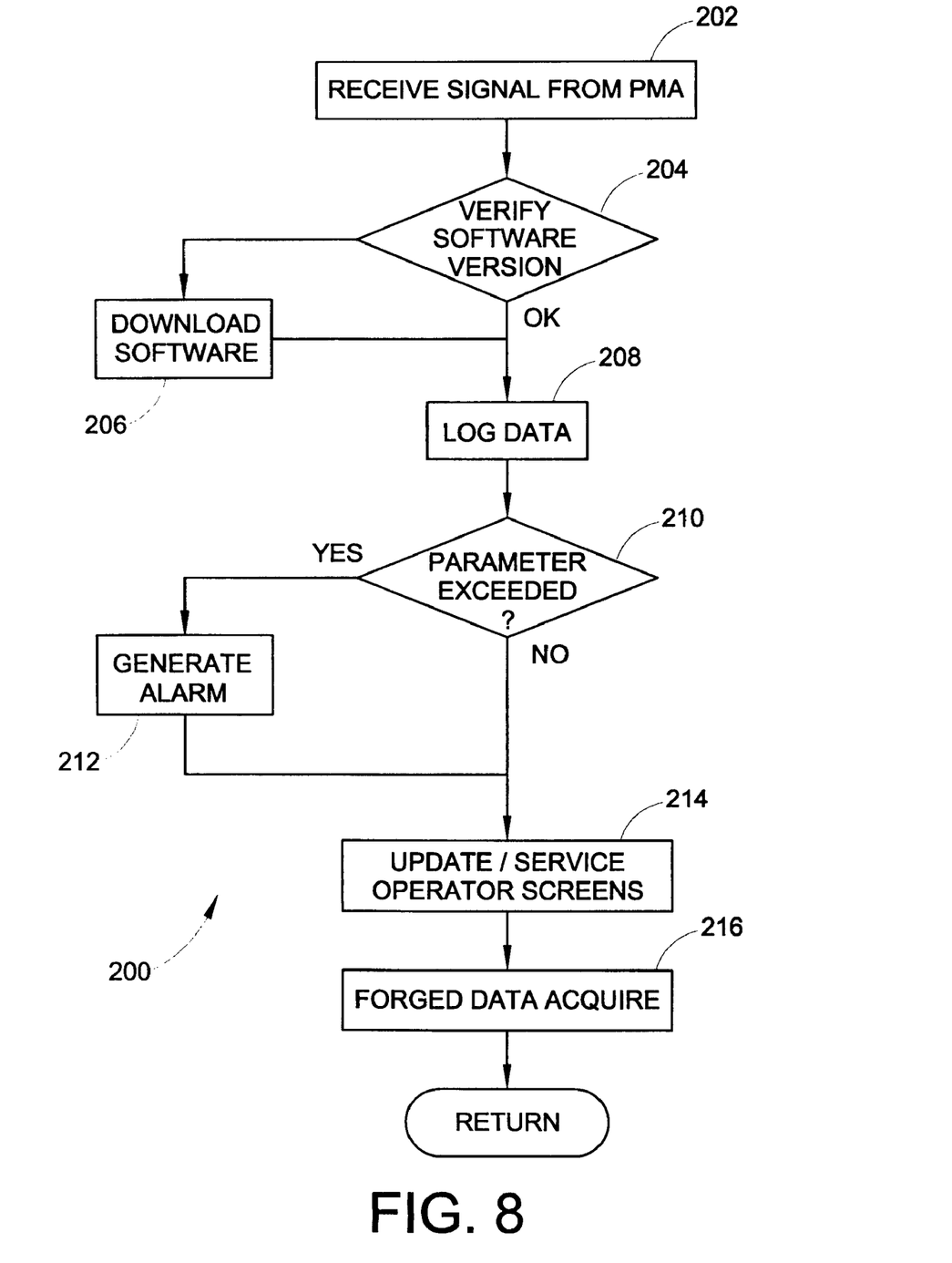
FIG. 8 is a flow chart of the method of operation of the monitoring network communicating with the portable monitoring apparatus executing the methods of FIGS. 5-7.

FIG. 8 illustrates the preferred method 200 executed by the monitoring network 16. As shown there, the method 200 includes a first step of receiving a signal from the portable monitoring apparatus 14. The signal received at step 202 is verified in step 204 to determine whether the software level of the first executable program 110 contained in the first memory portion 108 is up to date or whether it has been made obsolete by a newer operating system version. In the event that the operating system contained in the portable monitoring apparatus 14 is obsolete, the processor downloads an updated second executable program in step 206. In step 208, the control method 200 acquires all of the log data from the electronic monitoring circuit and determines whether any threshold values were exceeded. At step 210, if any threshold parameters were exceeded, an alarm is generated at step 212. Otherwise, the method 200 updates and services the operator screens at the central monitoring station 24 described below in connection with FIGS. 9-12. At step 216, any forced data acquisition commands received into the monitoring station 24 are serviced as may be necessary. Lastly, control returns at step 218 to a state waiting to receive the signal from the portable monitoring apparatus.

Figure 9:
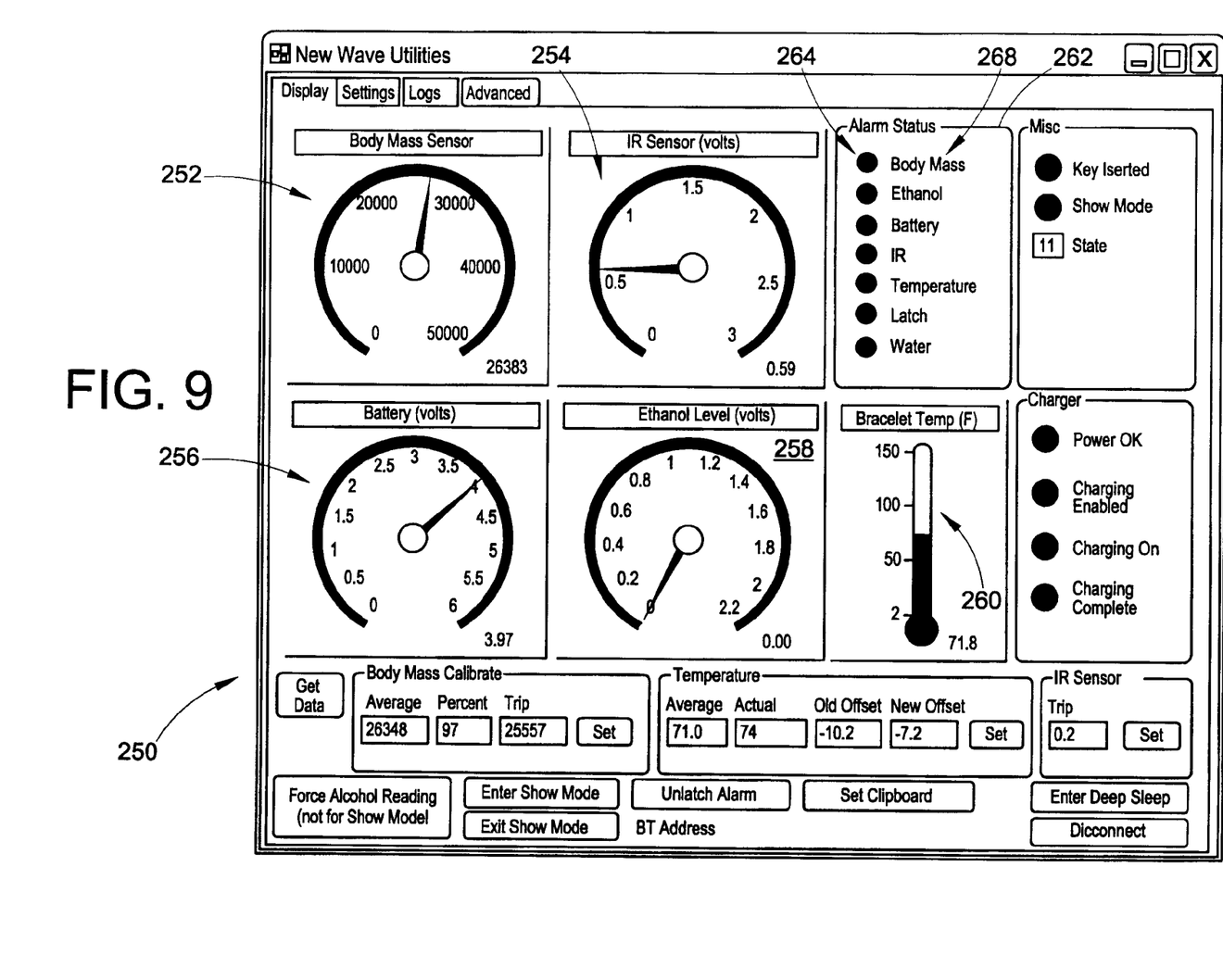
FIG. 9 is a view of a display screen provided at the central monitoring station.

FIG. 9 shows a display viewing and command screen of the subject system presented to operators at the central monitoring station 24 through the servers 28. As shown there, the display viewing and command screen includes dashboard representations of data acquired by the portable monitoring apparatus 14 including body mass data 252, infrared sensor data 254, battery voltage data 256, and alcohol/ethanol level data 258. A temperature gauge 260 is presented to give a visual indication of a body temperature data value acquired from the human substantially in real time. An alarm status panel 262 includes a set of buttons 264 presenting a color indication of a status of the alarm of each of the conditions 268 identified there including alarm status notices for an increase or decrease in the body mass value detected, a change in ethanol level detected, a battery voltage, infrared, temperature, a latch, and a water detection signal.

Figure 10:
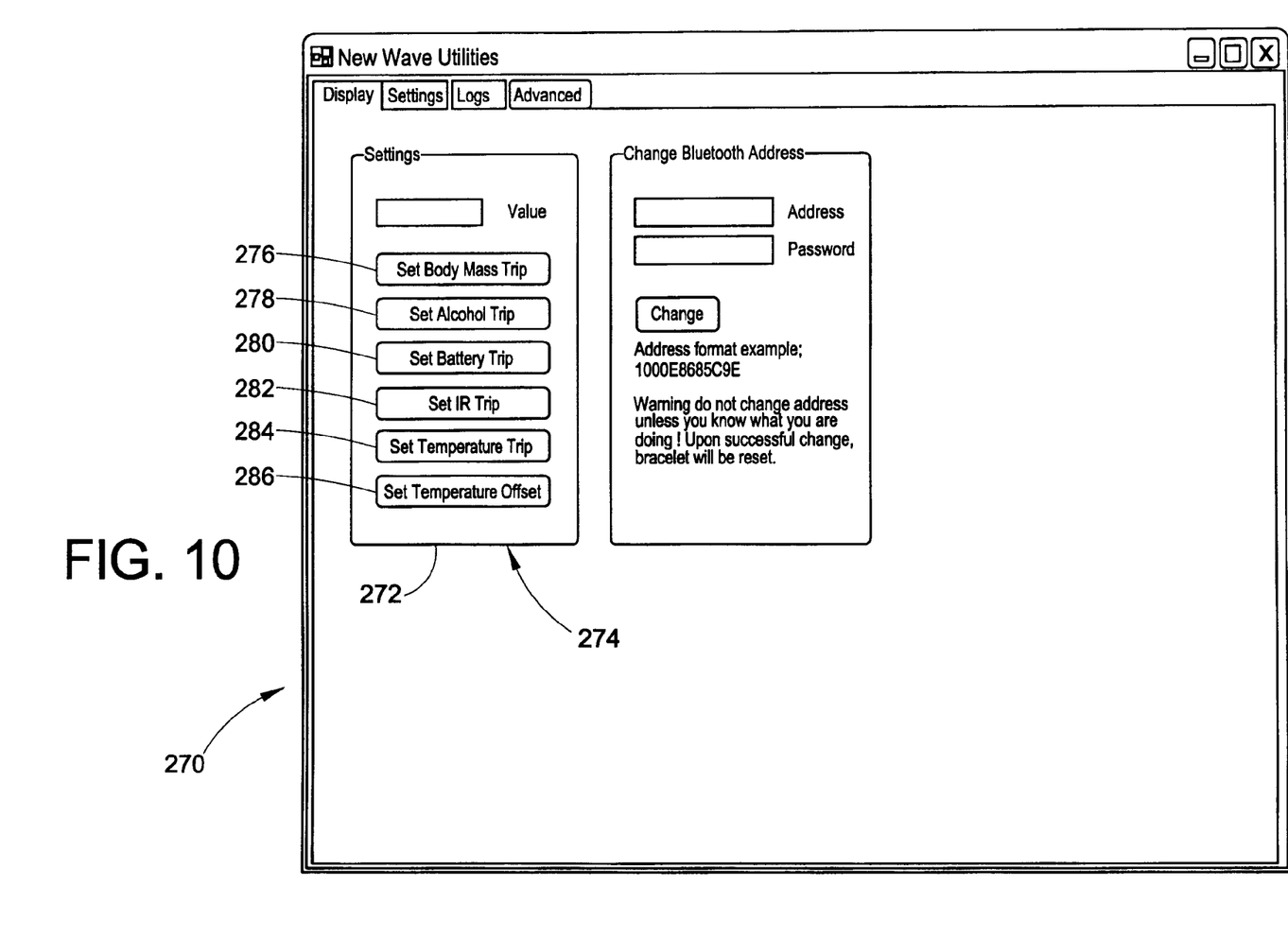
FIG. 10 is a view of a settings screen provided at the central monitoring stations.

FIG. 10 is a settings viewing and command screen 270 providing an interface for operators at the central monitoring station 24 on the server 28 to set the various alarm threshold values in a settings panel 272. Various settings buttons 274 are presented including a body mass trip point 276, an alcohol trip point 278, a battery trip point 280, an infrared trip point 282, a temperature trip point 284, and a temperature offset value 286.

Figure 11:
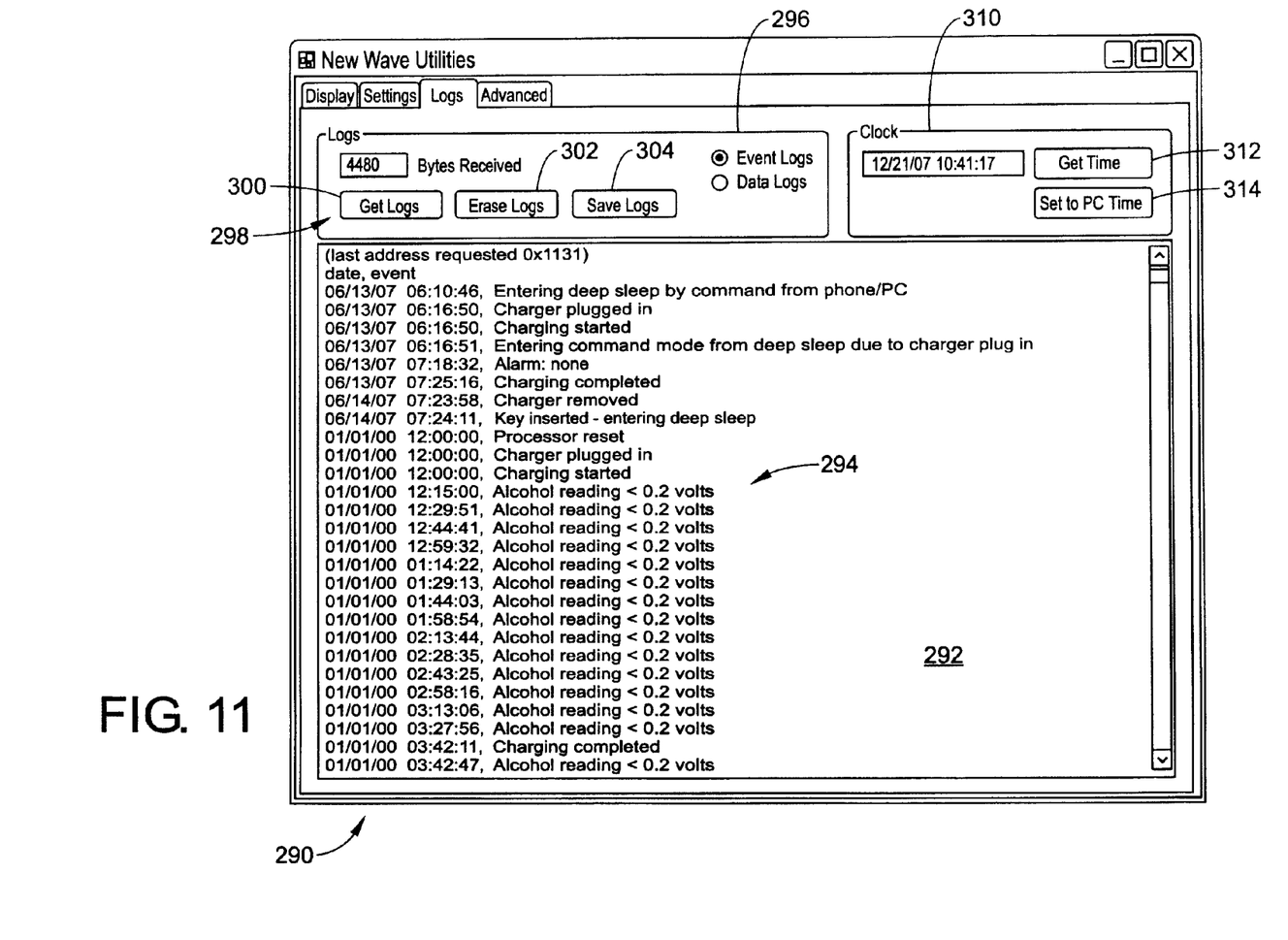
FIG. 11 is a view of a logs screen provided at the central monitoring station; and, FIG. 12 is a view of an advanced screen provided at the central monitoring station.

FIG. 11 shows a logs viewing and command screen 290 illustrating functionality provided by operators at the central monitoring station 24. The logs viewing and command screen 290 includes a display panel 292 containing visual representations of real time data logs 294 of values collected by the portable monitoring apparatus 14. In addition, a data log control panel 296 includes buttons 298 for retrieving 300, erasing 302, and saving 304 the data logs thus acquired. A clock setting panel 310 includes buttons 312 for setting 314 and getting 316 the time set or contained in the electronic monitoring circuit 100. The panel also enables retrieving the current time from one or more of the computers within the system and setting the time of the electronic monitoring circuit 100 accordingly.

Figure 12:
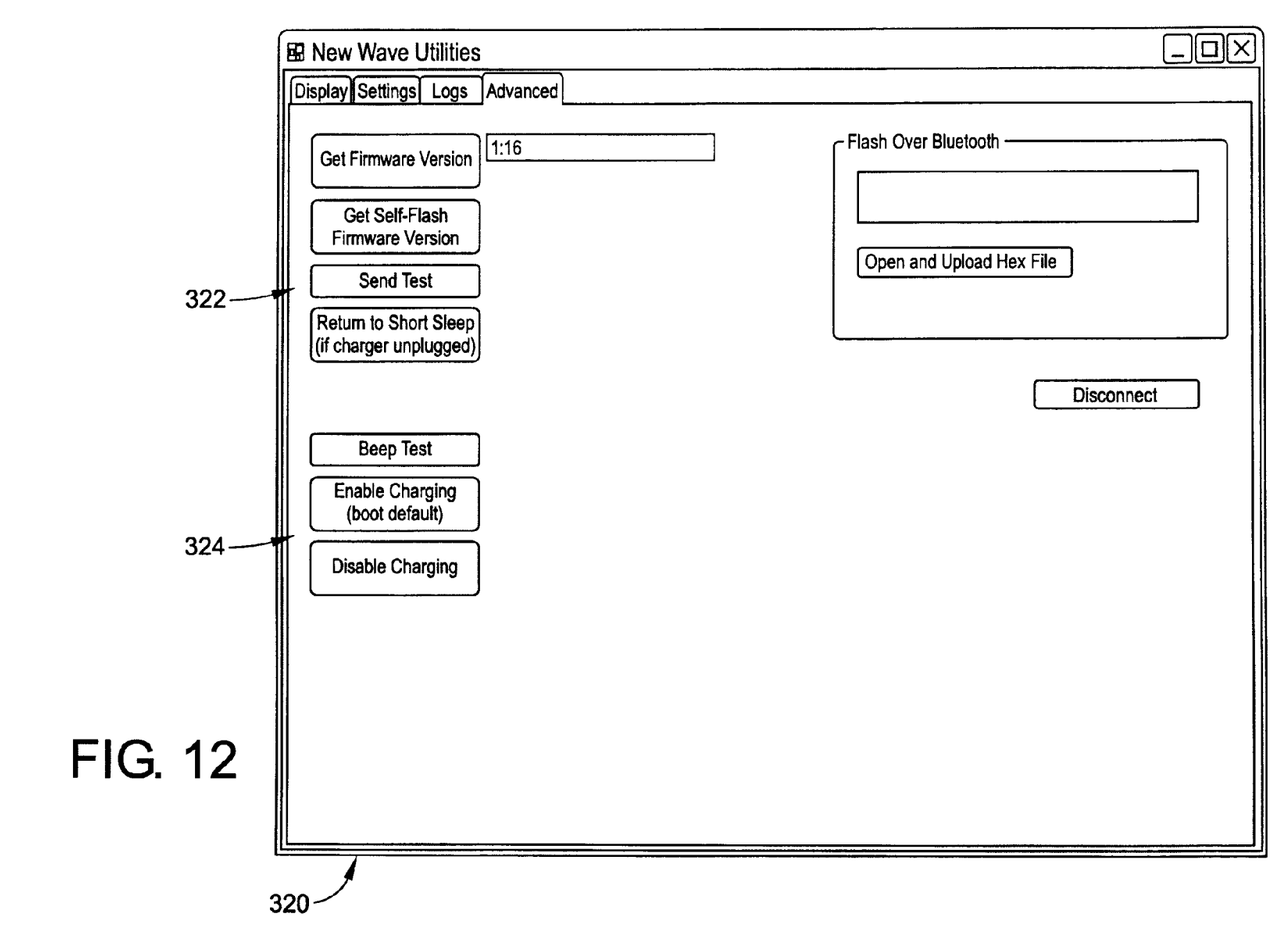

With reference next to FIG. 12, an advanced viewing and command screen 320 includes command buttons 322 for manipulating the executable program 110 contained in the electronic monitoring circuit 100. A first button executes a command protocol for querying the electronic monitoring circuit for a firmware version of the first executable program 110 contained therein. A second set of buttons 324 on the advanced viewing and command screen enable an audible alarm test and monitor the charging features of the circuit.

As described hereinabove, the present invention solves many problems associated with previous type devices. However, it will be appreciated that various changes in the details, materials and arrangements of parts, which have been herein described and illustrated in order to explain the nature of the invention, may be made by those skilled in the art without departing from the principle and scope of the invention, as expressed in the appended claims.

What is claimed is:

1. A monitoring system for monitoring a condition of an associated human, the monitoring system comprising:
   a bracelet having a housing and a strap for connecting the bracelet with a body part of the associated human being monitored;
   an electronic monitoring circuit disposed in said housing, the electronic monitoring circuit including:
      a first sensor for detecting a condition of said human being monitored and generating a first signal based on the detected condition,
      a first memory storing a first executable program defining a first control algorithm,
      a second memory storing data relating to said condition of the human being monitored,
      a processor operatively coupled with the first sensor and with the first and second memories, the processor being configured to execute the first executable program for controlling the electronic monitoring circuit according to said first control algorithm to generate condition data based on said first signal and relating to the detected condition of the human being monitored and store the condition data in the second memory,
      a transmitter operatively associated with the processor for selectively transmitting said condition data from the housing as a first transmitted signal, and
      a receiver operatively associated with the processor for selectively receiving a command signal as a first received signal; and,
   a monitoring network having at least one receiving circuit receiving said first transmitted signal and at least one transmitting circuit transmitting said command signal, the processor of said electronic monitoring system being responsive to the command signal from the monitoring network to execute a second executable program different from the first executable program for controlling the electronic monitoring circuit according to a second control algorithm different from the first control algorithm.

2. The monitoring system according to claim 1, wherein the first memory is configured to store said second executable program.

3. The monitoring system according to claim 2 wherein:
   said command signal includes said second executable program; and,
   the processor is configured to store the second executable program in the first memory.

4. The monitoring system according to claim 3 wherein the processor is configured to replace the first executable program in the first memory with the second executable program based on said command signal.

5. The monitoring system according to claim 4, wherein the monitoring network includes:
   a mobile cellular communication device adapted to be carried by the associated human being monitored; and,
   a central monitoring station having a database storing said condition data and said second executable program.

6. The monitoring system according to claim 1 wherein:
   the processor is configured to generate version data based on a predetermined property of said first executable program the transmitter is configured to transmit the version data from said housing; and,
   the monitoring system is configured to transmit said command signal based on a comparison between said version data received from the electronic monitoring circuit and a predetermined version data value stored in the monitoring network.

7. The monitoring system according to claim 6 wherein:
   said command signal transmitted from the monitoring network to the electronic monitoring circuit includes said second executable program; and,
   the processor is configured to replace the first executable program in the first memory with the second executable program based on said command signal, and further being configured to execute the second executable program for controlling the electronic monitoring circuit according to said second control algorithm.

8. The monitoring system according to claim 7, wherein the monitoring network includes:
   a mobile cellular communication device adapted to be carried by the associated human being monitored; and,
   a central monitoring station having a database storing said condition data, said condition data, and said second executable program.

9. A bracelet device for use in a monitoring system for monitoring a condition of an associated human, the bracelet device comprising:
   a housing including a base with i) a contact portion configured on a first side to engage skin of the associated human, and ii) a cavity portion having an opening on the first side, the opening selectively defining a closed sampling volume when the first side of the contact portion is held in contact with said skin of the associated human; and,
   an electronic monitoring circuit disposed in said housing, the electronic monitoring circuit including:
      a first sensor disposed at said sampling volume for detecting a condition of said human and generating a first signal based on the detected condition;
      a first memory storing a first executable program defining a first control algorithm;
      a second memory storing data relating to said condition of the human being monitored;
      a processor operatively coupled with the first sensor and with the first and second memories, the processor being configured to execute the first executable program for controlling the electronic monitoring circuit according to said first control algorithm to generate condition data based on said first signal and relating to the detected condition of the human being monitored and store the condition data in the second memory;
      a transmitter operatively associated with the processor for selectively transmitting said condition data from the housing as a first transmitted signal; and
      a receiver operatively associated with the processor for selectively receiving a command signal as a first received signal.

10. The bracelet device according to claim 9 wherein said cavity portion defines a closed sampling volume of about 1000 mm$^3$.

11. The bracelet device according to claim 9 wherein said first sensor is held in a spaced relationship from said skin of the associated human by said cavity portion.

12. The bracelet device according to claim 11 wherein the first sensor is spaced from said skin of the associated human by about 5-15 mm.

* * * * *